United States Patent [19]
Beins et al.

[11] Patent Number: 4,890,997
[45] Date of Patent: Jan. 2, 1990

[54] PHOTOPOLYMERIZATION IRRADIATION APPARATUS

[75] Inventors: Wolfgang Beins, Bad Homburg; Helmut Röhrig, Usingen; Ulrich Salz, Wehrheim; Lutz Gwinner, Mainz; Steffen Oppawsky, Bad Homburg, all of Fed. Rep. of Germany

[73] Assignee: Kulzer & Co. GmbH, Wehrheim, Fed. Rep. of Germany

[21] Appl. No.: 163,607

[22] Filed: Mar. 3, 1988

[30] Foreign Application Priority Data

Mar. 3, 1987 [DE] Fed. Rep. of Germany ....... 3707398

[51] Int. Cl.⁴ .......................... B05D 3/06; B29C 35/08
[52] U.S. Cl. ........................................ 425/174; 264/22; 264/279.1; 425/174.4; 427/4; 427/44; 427/55
[58] Field of Search ....................... 264/22, 137, 271.1, 264/279.1; 425/174, 434, 435, 174.4; 427/2, 4, 44, 55

[56] References Cited

U.S. PATENT DOCUMENTS

| 2,060,121 | 11/1936 | Richardson et al. | 425/434 |
| 2,300,495 | 11/1942 | Gerhart | 264/279.1 |
| 3,054,141 | 9/1962 | Hammesfahr | 425/174.4 |
| 3,965,277 | 6/1976 | Guditz et al. | 427/44 |
| 4,120,991 | 10/1978 | Ornstein et al. | 427/2 |
| 4,320,157 | 3/1982 | Von Hagens | 264/279.1 |
| 4,510,169 | 4/1985 | Linner | 427/4 |
| 4,576,796 | 3/1986 | McCormick | 427/4 |

OTHER PUBLICATIONS

"Einbettung von Knochen-Präparaten in Plexit 55" by K. Ziebolz, Der Praparator 19, pp. 99–106 (1973) [Embedding of Bone Preparations in Plexit 55].

"Anleitung zum Bau eines Beleuchtungsschrankes für die Polymerisation von Plexit 55" by K. Ziebolz. Der Präparator 21, pp. 5–7 (1975) "[Directions on Constructing an Irradiation Cabinet for Polymerization of Plexit 55"].

Primary Examiner—Jay H. Woo
Assistant Examiner—C. Scott Bushey
Attorney, Agent, or Firm—Frishauf, Holtz, Goodman & Woodward

[57] ABSTRACT

The irradiation apparatus for the photopolymerization of plastic embedding masses for histological preparations has a preparation support located in a housing and a plurality of irradiation lamps, with one lamp above and one lamp below the preparation support forming one lamp pair. In order to cure photopolymerizable embedding masses in a manner that does not harm the embedded preparations or specimens, and in particular to avoid an abrupt rise in the reaction heat, and so that a small number of irradiation lamps is sufficient, the preparation support is a rotary support plate having a plurality of light pervious preparation holding means located about its outer circumference, and the lamps are positioned such that in operation, the holding means sequentially pass in between the lamps of each lamp pair, and the centers of the holding means are located on a circle that is concentric with the axis of rotation of the support plate.

28 Claims, 8 Drawing Sheets

PHOTOPOLYMERIZATION IRRADIATION APPARATUS

REFERENCE TO RELATED DISCLOSURE

"Einbettung von Knochen-Präparaten in Plexit 55" by K. Ziebolz, Der Präparator 19, pp 99–106 (1973) [Embedding of Bone Preparations in Plexit 55].

"Anleitung zum Bau eines Beleuchtungsschrankes für die Polymerisation von Plexit 55" by K. Ziebolz, Der Präparator 21, pp 5–7 (1975) [Directions on Constructing an Irradiation Cabinet for the Polymerization of Plexit 55].

The present invention relates to irradiation apparatus for the polymerization of plastic embedding materials by light or photo effects, and more particularly to embedding histological specimens, preparations and slices, and tissue preparations, and especially to an apparatus for rapidly and uniformly photopolymerizing the embedding plastic substance.

BACKGROUND

Histological slices and the like can be embedded in plastics or resins. A typical plastic or resin suitable for such embedding is "plexit 55". "Plexit" is a trademark for a methacrylate embedding resin, described by the manufacturer, Rohm GmbH, of D-6100 Darmstadt 1, Federal Republic of Germany. Plexit 55, before being polymerized, is a thickly flowable or pourable resin which can be polymerized to form a solid crystal clear body by irradiation by light from a commercial fluorescent tube.

Usually, the irradiation lamps are used in pairs, one above and one below a support element for dishes in which the histological preparations are located, embedded in the liquid resin. Upon energizing the lamps, the liquid resin will polymerize due to the presence of light from the lamps.

In histology, which is the study of biological tissues, hard and soft tissues are examined under the microscope. The term "histology" is also understood to include an analytical technique with which morphological and histochemical tests can be performed on organic and inorganic hard and soft tissue samples. Since the tests must be performed under the microscope using thin slices approximately 1 micrometer thick, the tissue samples are first embedded in an embedding material, and a thin section or slice of the embedded preparation can then be prepared. As an alternative to a preparation embedded in a medium, slices of deep-frozen soft tissue specimens are also prepared.

In addition to the technique of embedding tissue specimens in plastic or resin, another technique currently used is to embed the specimens in paraffin.

One problem in embedding tissue preparations, especially soft tissue preparations, is how to harden or cure the embedding material with little heat buildup or bubble formation, so that soft tissues, in particular, will be prevented from undergoing any change.

The referenced articles in the literature describe the embedding of bone preparations, and apparatus therefor.

In the known irradiation cabinet, the embedded tissue preparations that are to be cured and that have for instance been put into a glass dish are placed on a glass work counter. Two sets of five fluorescent tubes (20 to 60 W in power) are connected in pairs, one set being located above and the other below the glass counter. The glass counter and the array of fluorescent tubes are mounted in a vertically adjustable manner, so that the spacing between the embedded preparation and the upper and lower fluorescent tubes can be varied. The pane of glass on which the chambers having the specimens to be embedded are placed has a thickness of approximately 10 to 15 mm. The irradiation cabinet is open at the back so that the reaction heat and vapors given off during the curing can dissipate. The up to five groups of lamps can be turned on and off as needed by switches. Since curing these plastics entails a considerable heat buildup, the light is switched off from time to time until the embedding material has cooled down. For monitoring the thermal development, a contact thermometer may be provided in the embedding material.

THE INVENTION

It is an object to provide an irradiation apparatus suitable for harmless curing of polymerizable embedding masses, in which, in particular, an abrupt increase in the reaction heat is avoided, and which requires only a small number of irradiation lamps.

Briefly, a support for specimen dishes is provided in the form of a rotatable support plate or turntable having a plurality of light pervious specimen holding means; the irradiation lamps are positioned such that in the operating state, the holding means pass sequentially between the lamps of each pair of lamps, and the centers of the holding means are located on a circle concentric with the axis of rotation of the support plate.

The arrangement has the advantage that a great number of specimens can be moved past the irradiation lamps. The support plate has light pervious specimen holding means on which the specimens that are to be cured are placed. Preferably, only these holding means are pervious to light, while the remainder of the support plate is impervious to light, so that the specimens to be cured can be irradiated by the upper and lower irradiation lamps in a targeted manner.

So that the prepared specimens can be uniformly cured from both above and below, each irradiation lamp under the support plate is associated with an irradiation lamp above the support plate. As the support plate rotates, the specimens are passed sequentially between the individual lamps of each pair; this provides the specimens with a kind of recovery time in between the individual irradiation phases, so that they can cool down.

For curing the embedding masses, a plurality of pairs of irradiation lamps are distributed about the circumference of the support plate. Preferably, on of these pairs emits radiation equivalent to daylight, while the other pairs, up to four in number depending on the size of the support plate, preferably emit blue light from the visible spectrum. The pair of irradiation lamps emitting radiation equivalent to daylight serves to prepolymerize or pre-jell the embedding masses, while the other pairs of lamps harden, or cure the pre-jelled masses.

DRAWINGS

FIG. 7 is a sectional view taken along the line VII—VII of

DETAILED DESCRIPTION

Figure 1:
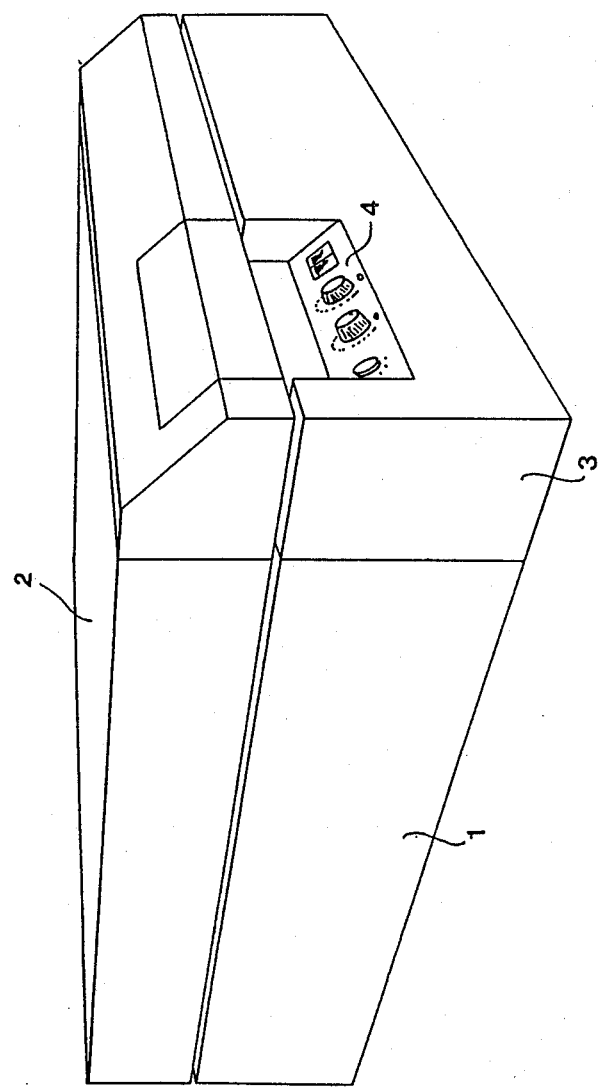
FIG. 1 is a perspective view of an irradiation apparatus.

As shown in FIG. 1, the irradiation apparatus has a flat housing 1, which is closed with a lid 2. A control and service panel 3 adjoins the front end of the housing 1. The lid 2 is formed such that it covers the control and service panel 3. The control and service panel 3 has a recess 4 in which the main switch and timer control elements are located such that they are readily accessible.

A rotary support plate or turntable 5 (see FIG. 2) is introduced into the housing 1. A plurality of preparation or specimen holding means in the form of recesses 6 are provided in the support plate 5. The centers of these recesses or specimen holding means are located on a circle that is concentric with the axis of rotation 7 of the support plate 5. The housing 1 is dimensioned such that the support plate 5 is immediately adjacent the side walls 8 of the housing. The support plate 5 has a center portion 9 having a centering depression 10.

Figure 2:
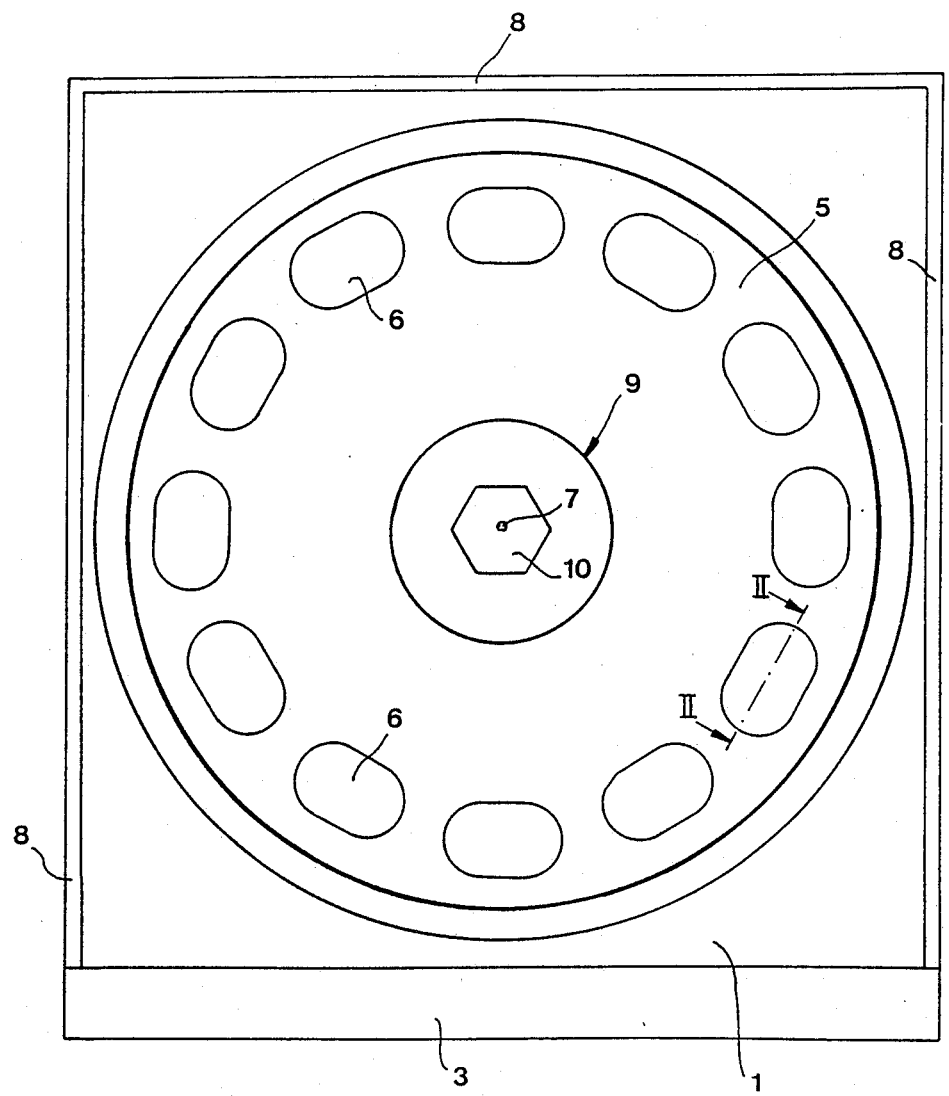
FIG. 2 shows a rotary support plate, or turntable, used in the irradiation apparatus of FIG. 1.
Figure 3:
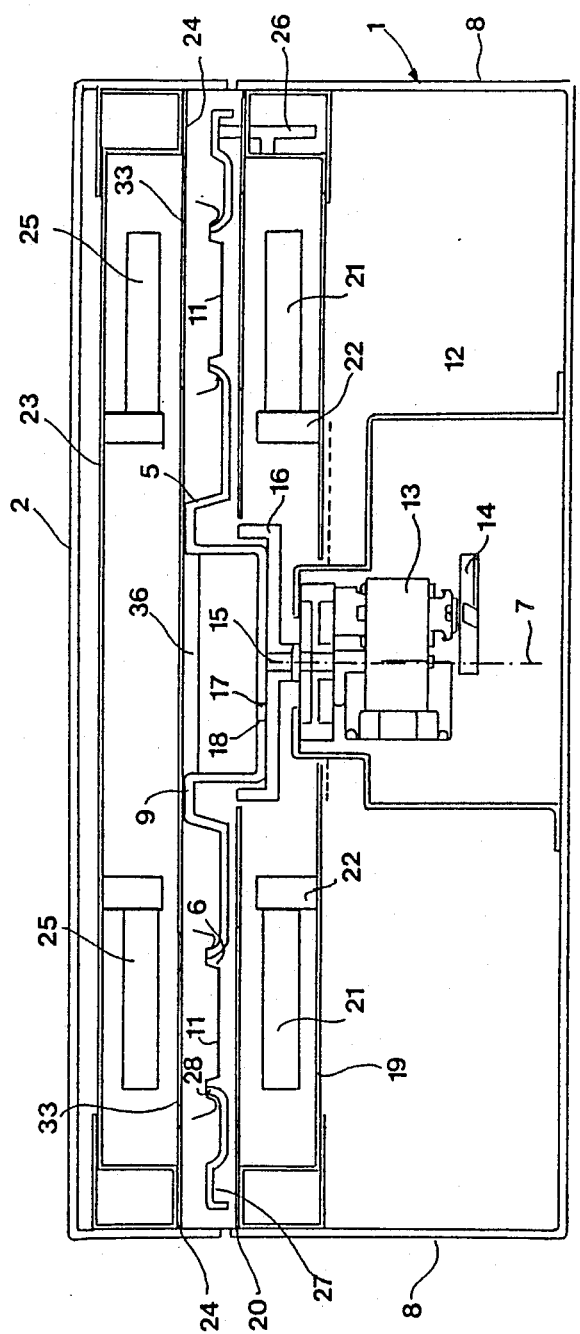
FIG. 3 is a longitudinal section through the irradiation apparatus in the vicinity of the drive shaft.

The support plate 5 shown in FIG. 2 is provided with twelve recesses 6 in the vicinity of its outer circumference, and as can be seen in FIG. 3 these recesses are each covered by an embedding mold or holding dish 11. In the middle of the housing 1, there is a drive motor 13 located in an intermediate housing 12. The drive motor 13 is a geared motor having a fan wheel 14 flanged onto it. In the embodiment shown in FIG. 3, a carrier plate 16 is mounted on the drive shaft 15 of the drive motor 13, and the middle portion 9 of the support plate 5 rests on the carrier plate 16. The carrier plate 16 carries the support plate 5 along with it via a stub 17 that engages a hole 18 in the middle portion 9 of the support plate 5.

A lower support plate 19, comprising a flat metal sheet with a reflective surface, and a lower sheet-metal lamp covering plate 20 are spaced apart from one another in the housing 1. Between the lower reflector 19 and the lamp covering plate 20 are a plurality of lower irradiation lamps 21, which are retained on the lower reflector 19 via bases 22.

In the lid 2 of the irradiation apparatus, in a laterally reversed arrangement as compared with the layout of the irradiation unit in the housing 1, are an upper reflector 23 and an upper sheet-metal lamp covering plate 24, and between them are upper irradiation lamps 25, which are secured to the upper reflector 23. One lower irradiation lamp 21 and one upper irradiation lamp 25 each are aligned with their axes toward one another such that the longitudinal axes 29 of the lamps coincide, in the projection seen from the top of the irradiation apparatus, the lower and upper lamps thus forming a pair of irradiation lamps. The support plate 5 is introduced between the lower lamp covering plate 20 and the upper lamp covering plate 25. The support plate 5, which has a diameter of 500 mm, is guided on its edge by a plurality of rollers 26 that are distributed about the circumference and engage an annular groove 27 on the underside of the support plate 5. At the same time, the support plate 5, which is molded from a thin slab of plastic, is reinforced at the edge by this annular groove 27. The support plate 5 is approximately 3 to 5 mm thick, at least in the vicinity of the recesses 6. The rim 28 of the recesses 6 protrudes beyond the top of the support plate 5. The holding dishes 11 rest on this rim 28, which protects them against slipping out of position.

Figure 4:
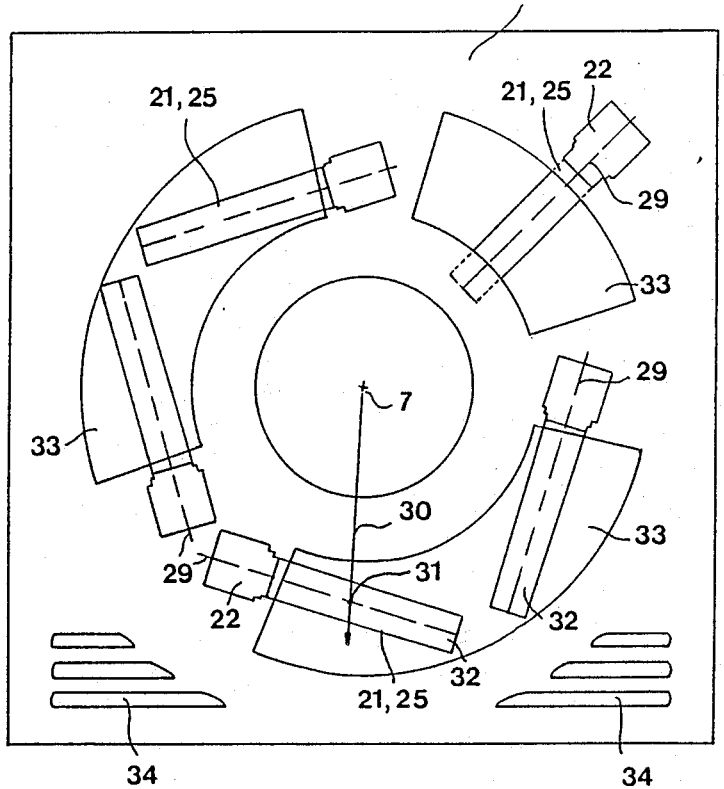
FIG. 4 shows a sheet-metal lamp covering plate, used in the irradiation apparatus, having an array of irradiation lamps.

As FIG. 4 shows, the irradiation apparatus is equipped with five pairs of irradiation lamps, the bases 22 of which are covered by the upper or lower lamp covering plate 20, 24. Of the five pairs of lamps, one pair—which in the example shown is the pair that is aligned with the longitudinal axes 29 of the lamps toward the axis of rotation 7 of the support plate 5—emits a spectrum corresponding to daylight. The lamps of the other four pairs of lamps 22 are fluorescent tubes that emit predominantly blue light.

For the daylight lamps, Osram "DULUX 7 W/41 Lumilux" bulbs, and for the blue light lamps, Osram "DULUX 9 W/71 Blue" bulbs (Osram Corporation, Newburgh, N.Y.), for example, are used.

The irradiation lamps 21, 25 emitting the blue light form tangents to the circle described by the centers of the preparation holding means (recesses 6) as they rotate with the support plate. Additionally, they are aligned such that the radius 30 that intersects the longitudinal axis 29 of the associated irradiation lamp 21, 25 in the middle, as indicated by the intersection point 31 for the lower irradiation lamp 21, 25, extends obliquely to the radius 30 of the circle. Of the four pairs of irradiation lamps 21, 25, each two pairs have their lamp ends 32 facing one another. With their axes, the four irradiation lamps oriented obliquely with respect to one another form a polygon. Because of how the lamps are arranged, there are three irradiation zones having corresponding openings 33 in the upper and lower lamp covering plates 20, 24. Arranging the irradiation lamps 21, 25 with their longitudinal axes 29 oriented obliquely to one another makes it possible to harden the embedding materials, which, as the support plate 5 revolves, sequentially pass in between the individual lamps of the pairs of lamps, without harming the specimens. Since the elongated irradiation lamps have a variable radiation intensity over their length, with the maximum being in the middle region, the embedding materials moved past them initially undergo a rise in radiation, which drops off again toward the opposite end of the lamp, with a zone of repose between each two adjacent pairs of lamps. In this way, the embedding materials are irradiated at intervals. Since the irradiation lamps 21, 25 that emit daylight serve solely to pre-jell the embedding materials, they can be aligned with their longitudinal axes 29 oriented toward the axis of rotation 7, as shown in FIG. 4. To dissipate the heat produced between the lamp covering plates 20, 24 and the reflectors 19, 23, a plurality of ventilation slits 34 are provided in the lamp covering plates 20, 24.

Figure 5:
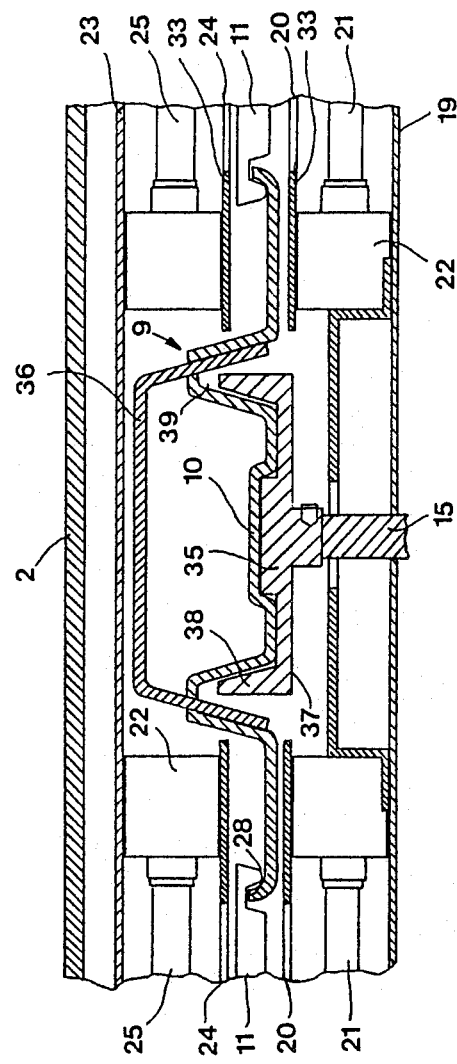
FIG. 5 is a sectional view, on a larger scale, of the support plate mounted on a drive stub.

As FIGS. 2 and 5 show, the support plate 5 is detachably mounted on the drive shaft 15, which has a centering stub 35 on its free end. For easier manipulation of the support plate 5, a handle 36 is secured in the vicinity of the middle portion 9. The centering stub 35 is formed as a hexagon, which interengages the complementarily formed centering depression 10. To make it easier to reinsert the support plate 5 after it has been removed from the irradiation apparatus, a ring element 37 with an encompassing rib 38 having an oblique side face on its inside is also secured to the centering stub 35. During insertion the support plate 5 is guided and at the same time stabilized in its position by means of a groove 39, adapted to this encompassing rib 38, in the middle portion 9 of the support plate 5. Once the support plate 5 is placed upon the ring element 37, it is rotated out of the most unfavorable position by a maximum of 60° (assuming a hexagonal centering stub 35) until it locks into position on the centering stub 35.

Figure 6:
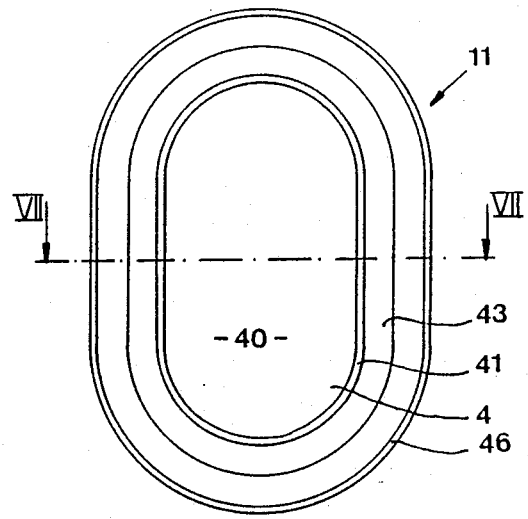
FIG. 6 is a plan view on a specimen holding dish.
Figure 7:
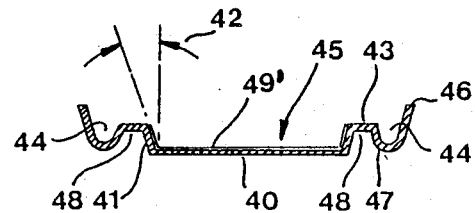
Figure 8:
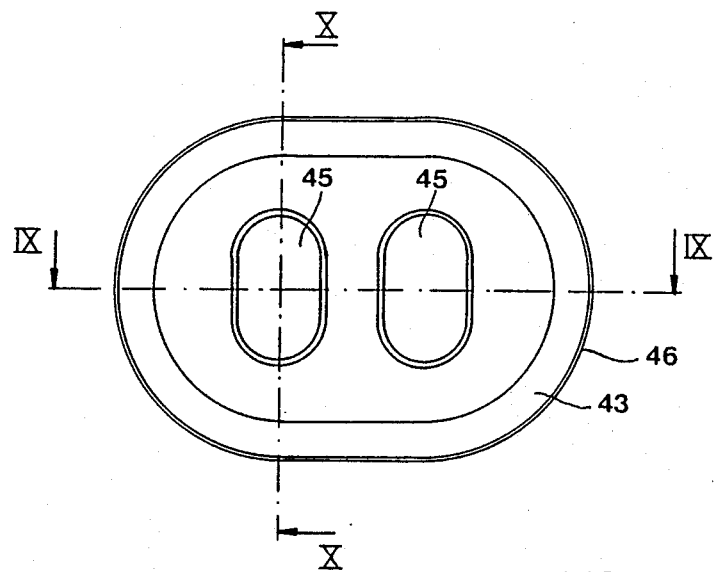
FIG. 8 shows a holding dish for two prepared specimens.
Figure 10:
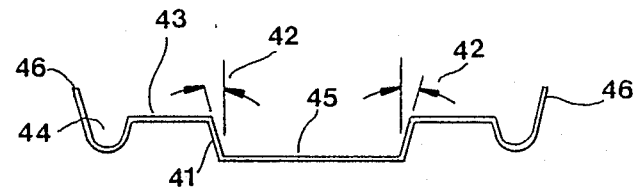
FIG. 10 is a cross section taken along the line X—X of FIG. 8.
Figure 11:
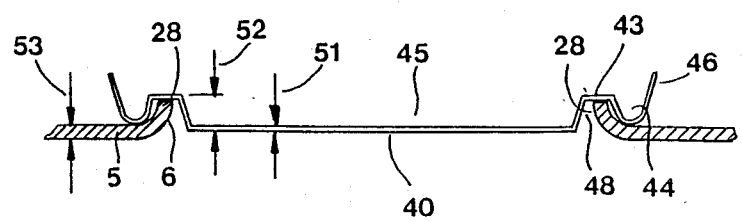
FIG. 11 is a cross section taken through the support plate along the line XI—XI of FIG. 2, with a holding dish as shown in FIGS. 6 and 7 emplaced in the support plate.

The holding dishes 11 (see FIGS. 6 and 7) inserted into the recesses 6 of the support plate 5 have an oval shape, in the examples shown, with a bottom 40 merging with outwardly slanting side faces 41. The slant of these side faces 41, which is indicated by the angle 42 in FIGS. 7 and 10, is 25°. Adjoining the rim of these side faces 41 is a horizontally extending surface 43, to which an encompassing channel 44 is attached. This encompassing channel 44 serves to receive excess embedding material poured into the cup-shaped region 45, so that from one holding dish to another, approximately the same thickness of cured embedding material is assured. The outer channel rim 46 protrudes beyond the inner channel rim 47; by means of this protruding outer channel rim 46 the holding dish 11 can easily be grasped with two fingers, and furthermore this raised outer channel rim 46 assures that no embedding material will run out of the holding dish 11. As FIG. 11 shows, the rim 28 of the recesses 6 that protrudes beyond the top of the support plate 5 lodges in the indentation 48 formed by the side faces 41, the horizontal surface 43 and the inner channel rim 47. Each holding dish 11 is centered via the respective rim 28 of the recess 6 engaging the indentation 48. In contrast to the holding dish shown in FIGS. 6 and 7, the holding dish of FIG. 8 and 9 has two cup-shaped regions 45, in each of which one specimen that is to be examined can be embedded.

Figure 9:
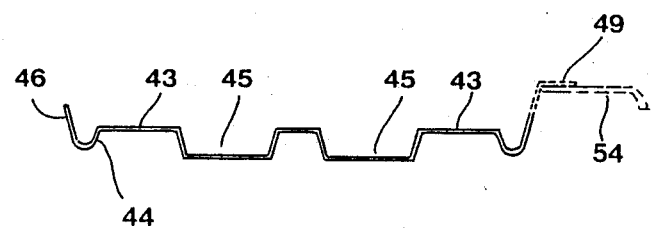
FIG. 9 is a longitudinal section taken along the line IX—IX of FIG. 8.

In FIG. 9, an additional support face 49, shown with broken lines, is provided on the outer channel rim 46; in contrast to the embodiment shown in FIG. 11, this support face can serve as a support rim in a manner corresponding to the horizontal surface 43.

The holding dishes 11 comprise acrylic glass or polyvinyl chloride, with an additional thin polyethylene film acting as a separation layer 49' (see FIG. 7), to enable easy removal of the cured embedding material from the holding dish 11.

The thickness 51 (FIG. 11) of the holding dish 11, at least in the vicinity of its bottom 40, is approximately 0.8 mm; the height 52 of the holding dish 11 is about 8 mm. The support plate 5 has a thickness 53 of 4 mm, at least in the vicinity of the recesses 6.

The support surface 49 shown in broken lines in FIG. 9 can also be used as a support surface for an adapter ring 54, which in turn is then placed upon the rim 28 of the recess 6 of the support plate 5. This lends wide variability in the dimensions of the individual holding dishes, which is of special interest if very small specimens are to be embedded.

In a preferred embodiment, the longitudinal axes of the lamp pairs 21, 25, or at least those used for the final curing, form parallels to the tangents of the circle on which the centers of the preparation holding means 6 revolve, which is coaxial with the axis of rotation of the support plate 5. With the irradiation lamps 21, 25, which are elongated fluorescent tubes 100 to 200 mm in length, arranged in this way, the radiation of the lamp is utilized over virtually its entire length. In an advantageous arrangement, in which the longitudinal axis of each lamp 21, 25 is oblique to the radius of the circle that intersects the longitudinal axis of each lamp in the middle of its length, the individual preparation holding means, or recesses 6, initially pass through a zone of low radiation intensity of the lamp, corresponding to the beginning or end of the lamp, before reaching the maximum intensity of the lamp pairs in the middle of their length. In this way, the holding means pass through zones having all the temperatures of the lamps. From one pair of lamps 21, 25 to the next, the radiation intensity first rises slowly, attains a maximum and then drops off once again After that, the preparation that is to be cured passes through a zone of repose, in which the embedding mass is cooled down, before it is irradiated once again in the vicinity of the next lamp pair. In this way, the preparations are irradiated at intervals, yet to attain this, there is no need to switch off the lamps or regulate their intensity. Depending on the number of irradiation intervals required and on the various irradiation times, a suitable number of pairs of irradiation lamps can be located along the support plate 5. The duration of irradiation can also be varied by varying the rotational speed of the support plate 5.

An arrangement in which the longitudinal axes of the pairs of lamps describe a polygon or a portion of a polygon has proved to be particularly suitable. With this orientation of the lamps, the largest possible portion of the length of the irradiation lamp is utilized for the irradiation. For uniform irradiation of the preparations from both the top and the bottom, the various lamps of one pair are positioned with their longitudinal axes such that in projection, the longitudinal axes coincide, as seen in the direction of the axis of rotation 7, that is, the normal to the surface of the support plate 5.

To keep the mass of the support plate 5 low, it is made of thin slab material, preferably having a thickness of from 3 to 5 mm. The support plates used in such equipment can have a diameter of up to 500 mm. To assure true concentric rotation of the support plates 5, it is guided in the vicinity of its outer circumference on at least two rollers 26 located on the housing; the at least two but preferably four rollers 26 may engage an annular groove 27 extending around the underside of the support plate; on the one hand this assures good guidance of the rollers, and on the other, the annular groove 27, which can be pressed in the form of a bead into the platform-like support plate, reinforces the support plate 5 at its edge.

To enable changing the support plate 5, it is detachably mounted on a drive shaft 15. The end of the drive shaft serves at the same time to center the support plate. An easily undone yet still positive connection between the support plate 5 and the drive shaft 15 can be made by forming the end of the centering stub 35 as a hexagon or Allen support plate, which engages a complementary centering depression 10 on the underside of the support plate 5. A hexagon such as this has the further advantage that when the support plate 5 is inserted into the irradiation apparatus, the support plate will need to be pivoted by a maximum angle of only 60°, no matter what its initial position, before positive engagement with the centering stub 35 is attained. Optionally, in order to reduce the necessary pivoting range of the support plate still further, a centering stub having more than six sides can be used.

Reflectors 19, 23 can be associated with the various lamps 21, 25 in order to aim the radiation of the lamps at the preparations to be irradiated. Preferably the reflectors 19, 23 comprise two flat plates, located above the upper lamps 25 and below the lower lamps 21 of the lamp pairs. At the same time, these reflector plates 19, 23 close off the irradiation chamber. The upper reflector plate 23 can advantageously simultaneously be the inside of a hinged lid 2 that closes the housing 1. Preferably the upper lamps of the pairs of lamps are also secured to this lid 2, so that when the lid 2 is opened the support plate 5 and the preparations placed upon it are freely accessible.

For a versatile irradiation apparatus in view of the different preparations to be embedded and for the sake of a targeted irradiation, the preparation holding means are in the form of recesses 6 in the support plate 5, and a cup-like holding dish 11 of light pervious material is placed in each of the holding means 6. As a result, different holding dishes 11 made of material pervious to light can be placed in the support plate 5, while the support plate 5 itself is impervious to light. When the irradiation apparatus is formed in this way, the individual holding dishes 11 can also be provided with the various preparations beforehand and then assembled on one support plate for irradiation.

The recesses 6 in the support plate 5, and hence the holding dishes 11 to be introduced into them, preferably are round or oval in shape, which results in a stable shape for the holding dish. In order to align the holding dish 11, which is approximately 5 to 15 mm high, centrally of the primary plane of the support plate 5, the rim 28 of the recesses 6 is made to protrude from the top of the support plate 5, on which the particular holding dish 11 rests with a rim adjoining its side face 41. The rims of the recesses 6 in the support plate 5 also reinforce the outer portion of the support plate 5; further provisions for such reinforcement are thus unnecessary. An overflow rim is also provided in this way, so that any embedding material running out of the holding dish 11 will be caught there.

A particularly secure position and simultaneous centering of the holding dish 11 in the recess 6 of the support plate 5 is attained by providing that each holding dish 11 has a rim 43 that is folded over toward its underside and overlaps the protruding rim 28 of the recess 6. In a preferred embodiment, a channel 44 adjoins the rim of the holding dish 11, on the one hand assuming the function of the aforementioned folded-over rim and on the other hand serving to catch any embedding material spilling out of the dish 11. As a result, a uniform quantity, or height, of embedding material from one holding dish 11 to another is assured. Once cured, any material that has spilled over into the channel can easily be broken off.

If the outer rim 46 is designed such that its height exceeds that of the inner rim 47 of the channel 44, it becomes easier to grasp and insert the holding dishes 11 into the recesses 6 of the support plate 5.

The wall thickness of the bottom of the holding dish 11 is preferably in the range from 0.5 to 1 mm.

To enable easy unmolding of the hardened embedding mass from the holding dishes 11, the side faces 41 adjoining the bottom 40 of the holding dish 11 slant outward, so that the dish that receives the embedding mass becomes wider toward the opening. An angle of inclination of from 5° to 30° of the side faces 41 to the vertical to the bottom 40 of the holding dish 11 has proved to be adequate.

In the event that very large recesses 6 are provided in the support plate 5, which are larger than the average dimensions of the various holding dishes 11, an adapter, for instance in the form of a ring element 37, can be inserted into the recess 6 and the holding dish 11 will then rest on its inner rim. This adapter is preferably made of material that is impervious to light.

The holding dish 11 is preferably manufactured from acrylic glass, also known as plexiglass, or polyvinyl chloride. To enable easy removal of the hardened embedding material from the holding dish, at least the inside of the bottom 40 and preferably the insides of the side faces 41 adjoining the bottom as well, are lined with a separation layer 49'. A separation layer in the form of a thin polyethylene film having a thickness of from 5 to 50 micrometers has proved to be satisfactory. This film is applied in the form of a protective film to the portions of the holding dish 11 that come into contact with the embedding material.

Various changes and modifications may be made, and features described in connection with any one of the embodiments may be used with any of the others, within the scope of the inventive concept.

We claim:

1. Photopolymerization irradiation apparatus for plastic-embedding masses, especially for histological specimens and preparations in a holding dish (11) comprising a rotary support plate (5) defining an axis of rotation (7);

light-pervious preparation holding means (6) for retaining a plurality of holding dishes (11) on circumferential regions of the support plate, with the centers of the holding dishes being located substantially on a circle concentric with said axis of rotation (7) of the rotary plate; and a plurality of radiation-generating lamp pairs (21, 25) in which the lamps of the pairs are positioned at circumferential intervals above and below said rotary plate and adapted to at least partially polymerize an embedding preparation, in each holding dish, which surrounds a specimen, and wherein said lamp pairs are located, with respect to the holding means (6) on the rotary support plate (5), such that, upon rotation of the support plate, the holding dishes (11) located on the holding mans sequentially pass alternately between the lamps of respective circumferentially positioned irradiation lamp pairs and through less-irradiated spaces in the circumferential intervals between lamps pairs, thereby enjoying a recovery period before further polymerization by a subsequent one of said lamp pairs.

2. The apparatus of claim 1 wherein the lamps are elongated and the longitudinal axes (29) of said lamp pairs (21, 25) form parallels to the tangents of the circle.

3. The apparatus of claim 1 wherein the lamps are elongated and the longitudinal axis (29) of some of said lamp pairs (21, 25) extends obliquely to the radius (30) of the circle that intersects this axis (29) of each lamp (21, 25) at the middle of its longitudinal extension.

4. The apparatus of claim 3 wherein the lamps are elongated and at least three pairs of lamps (21, 25) are provided, the longitudinal axes (29) of which describe a polygon.

5. The apparatus of claim 3 wherein the lamps are elongated and at least three pairs of lamps (21, 25) are provided, the longitudinal axes (29) of which describe a portion of a polygon.

6. The apparatus of claim 1 wherein the lamps are elongated and the longitudinal axes (29) of each lamp pair (21, 25) extend coincidentally in the projection in the direction of the axis of rotation (7).

7. The apparatus of claim 1 wherein said support plate (5) is guided in the vicinity of its outer circumference on at least two and preferably four rollers (26) located on a housing (1) surrounding said plate the at least two rollers (26) being positioned on two opposed sides of the support plate (5).

8. The apparatus of claim 6 wherein said rollers (26) engage an annular groove (27) encompassing the outer circumference of the support plate (5) on its underside.

9. The apparatus of claim 1, comprising means for supporting the support plate (5) on a drive shaft (15), a free end of which is formed as an interengaging centering stub (35).

10. The apparatus of claim 9 wherein the centering stub (35) is a polygon, which engages a centering depression (10) in the underside of the support plate (5).

11. The apparatus of claim 1 comprising at least one reflector (19, 23) associated with the lamps (21, 25).

12. The apparatus of claim 11 wherein said reflector (19, 23) is formed as a flat plate.

13. The apparatus of claim 11 wherein the reflector or reflectors (19, 23) form the inside of a hinged lid (2).

14. Photopolymerization irradiation apparatus for plastic-embedding masses, especially for histological specimens and preparations in a holding dish (11) comprising a rotary support plate (5) defining an axis of rotation (7);

light-pervious preparation holding means (6) for retaining a plurality of holding dishes (11) on circumferential regions of the support plate, with the centers of the holding dishes being located substantially on a circle concentric with said axis of rotation (7) of the rotary plate; and a plurality of radiation-generating lamp pairs (21, 25) in which the lamps of the pairs are positioned above and below said rotary plate and wherein said preparation holding means are recesses (6) in the support plate (5), into each of which a cup-shaped holding dish (11) of material pervious to light is inserted and wherein said lamp pairs are located, with respect to the holding means (6) on the rotary support plate (5), such that, upon rotation of the support plate, the holding dishes (11) located on the holding means sequentially pass between the lamps of respective circumferentially positioned irradiation lap pairs.

15. The apparatus of claim 14 wherein the recesses (6) in the support plate (5) have a round or oval outer contour.

16. The apparatus of claim 14 wherein a rim (28) of the recesses (6) protrudes beyond the top of the support plate (5).

17. The apparatus of claim 16 wherein each holding dish (11) has a rim (43, 47) folded over toward its underside, said rim overlapping the protruding rim (28) of the recess (6).

18. The apparatus of claim 17 wherein a channel (44) adjoins the rim of the holding dish (11).

19. The apparatus of claim 18 wherein an outer rim (46) of said channel (44) protrudes beyond an inner rim (47) of said channel.

20. The apparatus of claim 14 wherein said holding dish (11) has a wall thickness (51), at least in the vicinity of the bottom (40), of about 0.5 to 1 mm 21. The apparatus of claim 14 wherein said holding dish (11) has a height (52) of about 5 to 15 mm.

22. The apparatus of claim 14 wherein said holding dish (11) has side faces (41) adjoining its bottom (40) that are slanted outward.

23. The apparatus of claim 22 wherein the angle of inclination (42) of the side faces (41) to the vertical to the bottom (40) of the holding dish (11) is about 5° to 30°.

24. The apparatus of claim 14 wherein the thickness (53) of the support plate (5), at least in the vicinity of the recesses (6), is about 3 to 5 mm.

25. The apparatus of claim 14 wherein said holding dish (11) is mounted via an adapter (54) on the rim (28) of the recesses (6) of the support plate (5).

26. The apparatus of claim 14 wherein said holding dish (11) is of acrylic glass or polyvinyl chloride and has a separation layer (49') on at least the inside of its bottom (40).

27. The apparatus of claim 26 wherein said separation layer (49') is formed by a thin film, preferable a polyethylene film.

28. The apparatus of claim 27 wherein said film has a thickness of about 5 to 50 micrometers.

* * * * *